United States Patent [19]
Werbel

[11] 4,291,034
[45] Sep. 22, 1981

[54] 7-CHLORO-3-SUBSTITUTED ARYL-3,4-DIHYDRO-1,9(2H,10H) AND 10 HYDROXY ACRIDINEDIONEIMINES HAVING ANTIMALARIAL ACTIVITY

[75] Inventor: Leslie M. Werbel, Ann Arbor, Mich.

[73] Assignee: Warner Lambert Company, Morris Plains, N.J.

[21] Appl. No.: 132,362

[22] Filed: Mar. 20, 1980

[51] Int. Cl.³ .................... A61K 31/47; C07D 219/08
[52] U.S. Cl. ................................. 424/250; 424/257; 544/361; 546/103
[58] Field of Search ............... 546/103; 424/257, 250; 544/361

[56] References Cited

U.S. PATENT DOCUMENTS 2,647,901   8/1953   Archer ................................. 546/103
3,578,668   5/1971   Schnettler et al. ............. 544/361 X
3,947,449   3/1976   Dürckheimer et al. ............ 546/103

FOREIGN PATENT DOCUMENTS 46-31735   9/1971   Japan ................................... 546/106

OTHER PUBLICATIONS

Albert, "The Acridines", 2nd ed., St. Martin's Press, New York, 1966, pp. 310–315, 424–429.

Primary Examiner—Donald G. Daus
Assistant Examiner—Diana G. Rivers
Attorney, Agent, or Firm—Walter Patton

[57] ABSTRACT

7-Chloro-3-substituted aryl-3,4-dihydro-1,9-(2H,1OH) and 10-hydroxy-acridinedioneimines and their pharmaceutically acceptable salts and a process for preparing them are disclosed and claimed. The compounds are useful in the treatment of protozoan diseases.

12 Claims, No Drawings

7-CHLORO-3-SUBSTITUTED ARYL-3,4-DIHYDRO-1,9(2H,10H) AND 10 HYDROXY ACRIDINEDIONEIMINES HAVING ANTIMALARIAL ACTIVITY

BACKGROUND OF THE INVENTION

The compounds of the invention constitute a novel class of chemical compounds which are valuable chemotherapeutic agents particularly suitable for the prevention and treatment of protozoal infections. They are distinguished, for example, by a high activity against malaria parasites. The number of therapy resistant cases of malaria has considerably increased in the malaria infested areas of the world. Therefore, there is an urgent need for antimalarial drug which are effective against resistant strains.

SUMMARY AND DETAILED DESCRIPTION

The invention provides antiprotozoal compounds of the general formula (I)

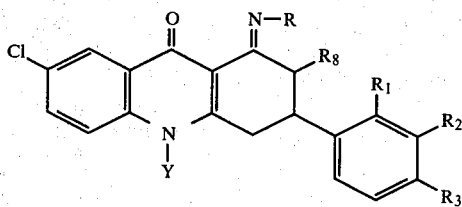

wherein Y is hydrogen or hydroxy; $R_1$ is hydrogen, fluorine, chlorine, bromine or iodine; $R_2$ and $R_3$ are hydrogen, fluorine, chlorine, bromine, iodine or trifluoromethyl;

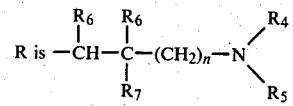

wherein n=0 to 5; $R_4$ and $R_5$ are hydrogen, alkyl containing one to four carbon atoms, $-CH_2-CH_2-OH$,

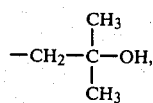

allyl, or $R_4$ and $R_5$ together are $(CH_2)_4$ to 5, or

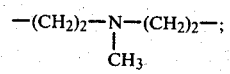

$R_6$ and $R_7$ are hydrogen, methyl, or ethyl; $R_8$ is hydrogen or methyl; and pharmaceutically acceptable acid addition salts thereof.

Preferred compounds of the invention have the formula

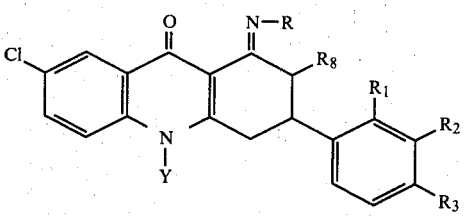

wherein Y is hydrogen or hydroxy; $R_1$ is hydrogen or chlorine; $R_2$ and $R_3$ are hydrogen, chlorine or trifluoromethyl;

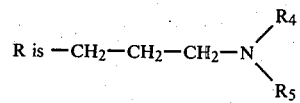

wherein $R_4$ and $R_5$ are hydrogen, $CH_3$ or $C_2H_5$; and acceptable acid addition salts thereof.

Examples of the preferred compounds of the present invention are:

7-chloro-3-(2,4-dichlorophenyl)-1-[[3-(dimethylamino)propyl]imino]-1,3,4,10-tetrahydro-9(2H)-acridinone;

7-chloro-3-(3,4-dichlorophenyl)-1-[[3-(dimethylamino)propyl]imino]-1,3,4,10-tetrahydro-10-hydroxy-9(2H)acridinone;

7-chloro-3-(3,4-dichlorophenyl)-1-[[2-(diethylamino)ethyl]imino]-1,3,4,10-tetrahydro-10-hydroxy-9(2H)acridinone;

7-chloro-1-[[3-(dimethylamino)propyl]imino]-1,3,4,10-tetrahydro-10-hydroxy-3-[4-(trifluoromethyl)phenyl]-9(2H)-acridinone;

7-chloro-3-(2,4-dichlorophenyl)-1-[[3-(dimethylamino)propyl]imino]-1,3,4,10-tetrahydro-10-hydroxy-9(2H)acridinone;

7-chloro-3-(3,4-dichlorophenyl)-1-[[2-(diethylamino)ethyl]imino]-1,3,4,10-tetrahydro-9(2H)acridinone;

7-chloro-1-[[3-(dimethylamino)propyl]imino]-1,3,4,10-tetrahydro-3-[4-(trifluoromethyl)phenyl]-9(2H)acridinone; and 7-chloro-1-[[3-(dimethylamino)propyl]imino]-1,3,4,10-tetrahydro-2-methyl-3-[4-(trifluoromethyl)phenyl]9(2H)-acridinone.

The invention also relates to a process for preparing the compounds of the formula I, which comprises treating a suitably substituted acridinedione II with the corresponding amine III in a polar or non-polar solvent such as methanol, ethanol, acetonitrile, benzene or N,N-dimethylformamide at temperatures from ambient to 100° C. for from 1 hr to 24 hrs exemplified by the equation:

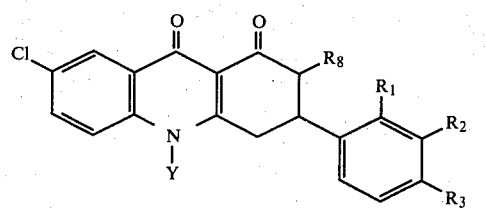

wherein the radicals R, $R_1$ to $R_3$, $R_8$ and Y have the meanings given above. Preferred conditions utilize alcoholic solvents under reflux for 1 hr.

The starting acridinediones of formula (II) where Y is OH may be prepared by the process described in U.S. Pat. No. 3,947,449 as illustrated by the following reaction scheme:

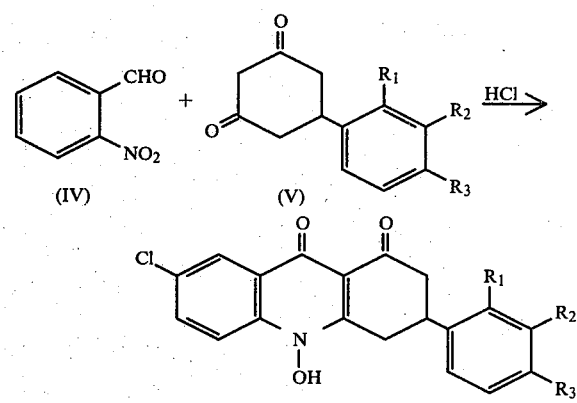

wherein $R_1$, $R_2$ and $R_3$ are as defined above.

Compounds IV and V are reacted in the presence of concentrated hydrochloric acid in a water-miscible organic solvent such as acetic acid at a temperature in the range of from 20° C. to 120° C., preferably 80° C. to 100° C. to form the desired acridinedione. The acridinedione of formula II where Y is H can be prepared by reducing the 10-hydroxy group of an acridinedione of formula II where Y is OH with phosphorus trichloride according to the following reaction scheme:

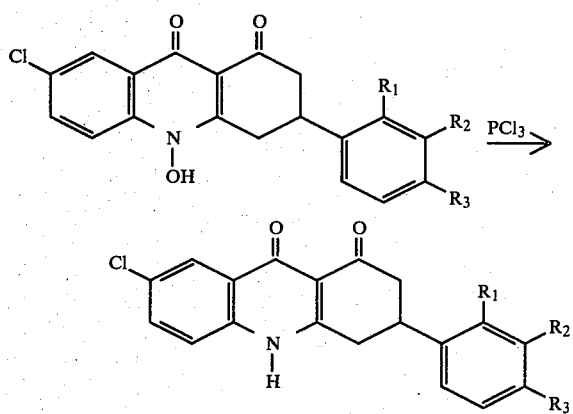

wherein $R_1$, $R_2$ and $R_3$ are as defined above.

Alternately the acridinediones of formula II where Y is H can be obtained by the route:

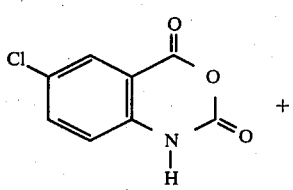

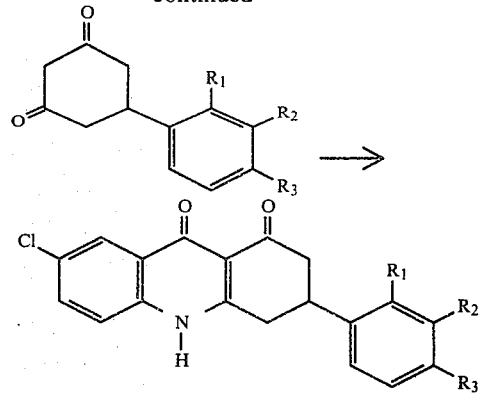

wherein $R_1$, $R_2$ and $R_3$ are as defined above.

The compounds (I) can be recrystallized from or triturated in a large variety of organic solvents set forth in Table I and II below. Because of their amphoteric nature, they form salts with acids and bases. Thus, for example, the hydrochlorides or hydrobromides can be prepared with hydrochloric acid or hydrobromic acid in alcohols.

Salts with bases are obtained, for example by dissolving 1 mole of the compound of the formula I with 1 mole of a strong base in water or alcohols and carefully concentrating this solution or lyophilizing it. As bases, there may be used all strong non-toxic, physiologically acceptable bases, for example, sodium hydroxide, potassium hydroxide, calcium hydroxide or tetramethylammonium hydroxide.

The compounds of the formula I may be administered perorally or parenterally in doses ranging from 2.5 to 100 mg/kg of body weight. As antimalarial drugs, dosage unit forms such as dragees or capsules for oral administration or solutions and suspensions, respectively, for injections, each containing 100 to 400 mg of active substance are preferred. Such dosage units are administered once to three times daily depending on the condition of the patient.

For oral administration, there may be used in particular tablets, dragees, capsules, powders or granules which contain the active substances together with the usual excipients and adjuvants such as starch, cellulose powder, talcum, magnesium stearate, sugar, gelatin, calcium carbonate, finely divided silicic acid, carboxymethyl-cellulose or similar substances.

For parenteral administration, in particular for intramuscular injections, there may be used sterile suspensions, for example oily suspensions prepared with the use of sesame oil, castor oil or synthetic triglycerides, optionally with simultaneous use of surface-active substances such as sorbitan fatty acid esters. Furthermore, there may also be used aqueous suspensions prepared, for example with the use of ethoxylated sorbitan fatty acid esters, optionally with addition of thickeners such as polyethylene glycol or carboxymethyl-cellulose.

Test Procedure

The compounds of the invention were tested against a normal drug-sensitive strain of P. berghei in mice by the parenteral route. A test description is contained in: T. S. Osdene, P. B. Russell and L. Rane, J. Med. Chem., 10, 431 (1967). The compounds were dissolved or suspended in sesame or peanut oil and were administered to mice in a single subcutaneous dose 72 hrs post infection. Extension of the mean survival time of the treated mice is interpreted as evidence of antimalarial activity. Animals that survive to 60 days are listed as C in Table I and II. The mean survival time of infected control mice ranges from 6.1–6.3 days. Numbers in parentheses in the table indicate extension of survival time over the controls as an average for those animals of the 5 animal group which did not survive to 60 days. Animals which expired before 6.1 days are designated by the letter T.

TABLE I

Effects of Imines of 7-Chloro-3-aryl-3,4-dihydro-10-hydroxy-1,9(2H,10H)-acridinediones Against Trophozoite-Induced P. berghei in Mice. Compounds prepared by the process of Examples 1 and 2.

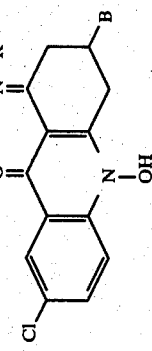

| NR | R | 640 | 320 | 160 | 80 | 40 | 20 | mp °C. | Recryst. Solvent |
|---|---|---|---|---|---|---|---|---|---|
| N(CH₂)₃N(Me)₂ | 3,4-Cl₂—C₆H₃ | 5C | 5C | 5C | 3C(17.2) | 3C(12.7) | 7.1 | 208–210 | EtOH |
| N(CH₂)₃N(Me)₂ | 4-CF₃—C₆H₄ | 4T,1C | 3T,2C | 2T,3C | 4C | 5C | 5C | 130–135 (0.4H₂O) | C₆H₆—cyclohexane |
| N(CH₂)₂N(Et)₂ | 3,4-Cl₂—C₆H₃ | 5C | 5C | 5C | 3C(12.7) | 3C(8.8) | 1C(10.5) | 212–213 | EtOH |
| N(CH₂)₃N(Et)₂ | 3,4-Cl₂—C₆H₃ | 5C | 5C | 4C(12.7) | 2C(11.7) | 8.5 | 5.3 | 182–184 | EtOAc |
| N(CH₂)₃N(Me)₂ | 3-CF₃—C₆H₄ | 5C | 5C | 4C(12.4) | 9.6 | 6.9 | 4.8 | 134–136 | C₆H₆—cyclohexane |
| N(CH₂)₇N(Me)₂ | 3,4-Cl₂—C₆H₃ | 5C | 5C | 5C | 11.3 | 6.5 | — | 155 | tritd Et₂O |
| N(CH₂)₃N(CH₂)₅ | 3,4-Cl₂—C₆H₃ | 5C | 5C | 4C(8.7) | 9.2 | 5.9 | — | 195–197 | tritd EtOAc |
| NCH(CH₃)(CH₂)₃N(Et)₂ | 3,4-Cl—C₆H₃ | 5C | 5C | 5C | 1C(6.1) | 1C(6.1) | — | 150–154 (2HCl) | tritd Et₂O |
| N(CH₂)₃N(Me)₂ | C₆H₅ | 5C | 8.8 | 4.2 | 1.2 | 0.6 | — | 122–126 (H₂O) | C₆H₆—cyclohexane |
| N(CH₂)₃N(Me)₂ OH | 3,4-Cl₂—C₆H₃ | — | 5C | 5C | 4C(8.0) | 8.2 | 6.3 | 175–179 | tritd cyclohexane |
| N(CH₂)₂N(Et)CH₂C(CH₃)₂ | 3,4-Cl₂—C₆H₃ | 5C | 1C(13.0) | 2C(9.7) | 1C(6.3) | 1C(5.3) | 3.6 | 196–197 | EtOH |
| N(CH₂)₂N[CH₂CH(CH₃)₂]₂ | 3,4-Cl₂—C₆H₃ | 5C | 5C | 4C(10.6) | 1C(7.9) | 5.6 | 1.2 | 112–115 (0.8H₂O) | tritd CH₃CN |
| N(CH₂)₃N(CH₂CH₂OH)₂ | 3,4-Cl₂—C₆H₃ | 5C | 4C(11.6) | 3C(9.6) | 1C(7.9) | 6.6 | 2.0 | 187–188 | tritd EtOH |
| N(CH₂)₂NHCH₂CH₂OH | 3-CF₃—C₆H₄ | 5C | 5C | 5C | 1C(9.4) | 2C(5.9) | 3.0 | 198–200 | tritd Et₂O |
| N(CH₂)₂NHCH₂CH=CH₂ | 3-CF₃—C₆H₄ | 5C | 5C | 5C | 1C(10.9) | 6.8 | 5.6 | 167–168 | n-heptane |
| NCH₂CH(Et)NHBu | 3-CF₃—C₆H₄ | 5C | 5C | 3C(11.6) | 7.0 | 1C(9.6) | 5.4 | 169.5–170.5 | tritd n-heptane |
| N(CH₂)₂N(Bu)₂ | 3,4-Cl₂—C₆H₃ | 5C | 5C | 4C(10.6) | 1C(9.1) | 9.4 | 4.4 | 142–144 (0.3H₂O) | EtOAc |
| N(CH₂)₃NHBu | 3,4-Cl₂—C₆H₃ | 5C | 5C | 3C(10.1) | 1C(9.6) | 8.6 | — | 87–90 (0.5H₂O) | CH₃CN |
| N(CH₂)₃N(Et)CH₂CH₂OH | 3,4-Cl₂—C₆H₃ | 5C | 5C | 5C | 10.6 | 7.4 | — | 200–202 | tritd EtOAc |
| N(CH₂)₃N⟨NMe⟩ | 3,4-Cl₂—C₆H₃ | 5C | 4C(13.6) | 4C(14.6) | 2C(10.3) | 1C(9.6) | 4.0 | 197–199 | EtOAc |
| NCH₂C(CH₃)₂N(Et)₂ | 3-CF₃—C₆H₄ | 5C | 5C | 4C(8.6) | 9.2 | 1C(11.9) | 4.0 | 168–171 | C₆H₆ |
| NCH₂CH(CH₃)N(Me)₂ | 3-CF₃—C₆H₄ | 2C,3T | 5C | 3C(9.6) | 6.0 | 6.2 | — | 165–166 (.25H₂O) | tritd n-heptane |
| N(CH₂)₃N(CH₂)₄ | 3-CF₃—C₆H₄ | 4C(25.6) 2C,3T | 5C | 4C(9.6) | 8.0 | 6.6 | — | 191–192 | toluene |
| N(CH₂)₂N(CH₂)₄ | 4-CF₃—C₆H₄ | 4C,1T | 4C,1T | 4C,1T | 5C | 2C(10.8) 5C | 1C(10.5) | 182–183 | CH₂Cl₂—toluene-hexane |
| N(CH₂)₃N(CH₂)₄ | 4-CF₃—C₆H₄ | 3C,2T | 3C,1T | 5C | 2C(10.8) | 2C(10.8) | 1C(11.0) | 182–183 | CH₂Cl₂—toluene-hexane |
| N(CH₂)₃N(Et)₂ | 4-CF₃C₆H₄ | 5T | 2C,3T | 2C,3T | 2C,3T | 3C(16.8) | 2C(10.1) | 155–157 | CH₂Cl₂—toluene-hexane |
| N(CH₂)₄N(Et)₂ | 4-CF₃C₆H₄ | 4T | 4C | 5C | 5C | 4C(10.5) | 2C(14.0) | 122–125 | CH₂Cl₂—cyclohexane |
| N(CH₂)₃N(CH₂CH₂OH)₂ | 4-CF₃—C₆H₄ | 5C | 5C | 5C | 1C(9.5) | 4C(14.8) | 2C(12.0) | 87–90 | CH₂Cl₂—Et₂O |

TABLE I-continued

Effects of Imines of 7-Chloro-3-aryl-3,4-dihydro-10-hydroxy-1,9(2H,10H)-acridinediones Against Trophozoite-Induced *P. berghei* in Mice. Compounds prepared by the process of Examples 1 and 2.

| NR | R | \multicolumn{5}{c|}{Change in mean survival time or survival beyond 60 days (C) after single s.c. dose, mg/kg} | mp °C. | Recryst. Solvent |
|---|---|---|---|---|---|---|---|---|
| | | 640 | 320 | 160 | 80 | 40 | 20 | | |
| N(CH₂)₂N(CH₃)₅ | 4-CF₃—C₆H₄ | 1C,4T | 5C | 5C | 3C(12.0) | 3C(10.0) | 8.5 | 194-195 | CH₂Cl—Et₂O |
| NCH₂C(CH₃)₂CH₂N(Et)₂ | 4-CF₃—C₆H₄ | 3C,2T | 5C | 5C | 4C(12.5) | 3C(11.2) | 3C(13.0) | 172-173 | CH₂Cl₂—Et₂O |
| N(CH₂)₂NHCH₂CH=CH₂ | 4-CF₃—C₆H₄ | 5T | 5T | 5C 2C,3T | 1C,3T | 2C(8.4) | 7.8 | 116-119 | EtOAc-Et₂O |
| N(CH₂)₃NHCH₂CH₂OH | 4-CF₃—C₆H₄ | 1C,4T | 4C,1T | 5C | 5C | 3C(10.7) | 6.4 | 142-145 | CH₂Cl₂—toluene |
| NCH₂CHCH₂CH₃ \| NH(CH₂)₃CH₃ | 4-CF₃—C₆H₄ | 4C,1T | 5C | 5C | 4C | 2C(7.7) | 2C(6.0) | 162-164 | CH₂Cl₂—i-Pr₂O |
| N(CH₂)₃N(CH₃)₂ | 2,4-Cl₂—C₆H₃ | 4C,1T | 5C | 5C | 5C | 5C | 4C(10.6) | 172-174 | CH₂Cl₂—i-Pr₂O |
| N(CH₂)₃N(CH₃)₂ (2-CH₃) | 3,4-Cl₂—C₆H₃ | 5C | 4C | 5C | 4C(22.0) | 1C(8.8) | 6.8 | — | — |
| N(CH₂)₃N(CH₃)₂ (2-CH₃) | 2,4-Cl₂—C₆H₃ | — | — | — | — | — | — | 192-5 | CH₃CN |
| N(CH₂)₃N(CH₃)₂ | 4-CF₃—C₆H₄ | — | — | — | — | — | — | 195-7 | Et₂O—Petr . Et₂O |

TABLE II

Effects of Imines of 7-Substituted-3,4-dihydro-3-aryl-1,9(2H,10H)-acridinediones Against Trophozoite-Induced *P. berghei* in Mice. Compounds prepared by the process of Examples 3 and 4.

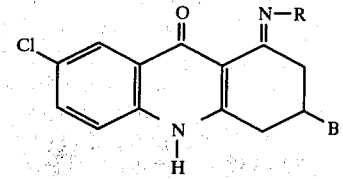

| R | B | \multicolumn{6}{c}{Change in mean survival time or survival beyond 60 days (C) after single s.c. dose, mg/kg} | mp °C. | Rcryst. Solvent |
|---|---|---|---|---|---|---|---|---|---|
| | | 640 | 320 | 160 | 80 | 40 | 20 | | |
| (CH$_2$)$_3$N(CH$_3$)$_2$ | 3,4-Cl$_2$—C$_6$H$_3$ | 5C 2C, | 5C | 5C | 4C(11.8) | 3C(9.8) | 9.2 3C | 216–219 | EtOH |
| (CH$_2$)$_3$N(CH$_3$)$_2$ | 4-CF$_3$—C$_6$H$_4$ | 3T | 2C,2T | 3C,1T | 5C | 5C | (10.4) | 211–213 | EtOH |
| (CH$_2$)$_3$N(CH$_3$)$_2$ | 3-CF$_3$—C$_6$H$_4$ | 5C | 5C 3C | 5C | 1C(14.4) | 6.6 | — | 205–207 | EtOH |
| (CH$_2$)$_2$N(C$_2$H$_5$)$_2$ | 3,4-Cl$_2$—C$_6$H$_3$ | 5C | (20.0) | 5C | 4C(8.0) | 4C(8.0) | 2C(9.3) | 273–275 (dec) | DMF |
| CH$_3$<br>\|<br>CH$_2$CHN(CH$_3$)$_2$ | 4-CF$_3$—C$_6$H$_4$ | 5C | — | 5C | — | 5C | — | 275–276 | EtOH |
| (CH$_2$)$_2$N(C$_2$H$_5$)$_2$ | 4-CF$_3$—C$_6$H$_4$ | 5C 3C | — | 5C 3C | — | 3C(17.6) | — | 233–235 | EtOH |
| (CH$_2$)$_7$N(C$_2$H$_5$)$_2$ | 4-CF$_3$—C$_6$H$_4$ | 5C (0.1) | — | (23.1) | — | 4C(9.6) | — | 148–152 | cyclohexane |
| CH(CH$_2$)$_3$N(C$_2$H$_5$)$_2$<br>\|<br>CH$_3$ | 4-CF$_3$—C$_6$H$_4$ | 2C (3.3) | — | 5C | — | 5C | — | 141–143 | CH$_3$CN |
| (CH$_2$)$_4$N(C$_2$H$_5$)$_2$ | 4-CF$_3$—C$_6$H$_4$ | 5C | 5C | 5C 2C | 5C | 4C(13.6) | 2C(9.9) | >300° (0.5H$_2$O) | EtOH |
| (CH$_2$)$_3$N(CH$_3$)$_2$ | 2-Cl—C$_6$H$_4$ | 5C 4C, | — 4C | (11.3) | 6.3 | 5.6 | — | 154–157 | EtOH |
| CH$_2$C(CH$_3$)$_2$CH$_2$N(C$_2$H$_5$)$_2$ | 4-CF$_3$—C$_6$H$_4$ | 1T 4C, | (49.6) | 5C | 4C(13.6) | 5C | 2C(8.6) | 172–174 | EtOH |
| N(CH$_2$)$_3$N(CH$_3$)$_2$ (2-CH$_3$) cis | 3,4-Cl$_2$—C$_6$H$_3$ | 1T | 5C | 5C | 4C(10.7) | 1C(10.5) | 5.5 | 147–150 | CH$_3$CN |
| N(CH$_2$)$_3$N(CH$_3$)$_2$ (2-CH$_3$) trans | 3,4-Cl$_2$—C$_6$H$_3$ | — | 5C | 5C | 2C(10.7) | 1C(7.2) | 5.3 | 229–231 | EtOH |
| N(CH$_2$)$_3$N(CH$_3$)$_2$ (2-CH$_3$) cis | 4-CF$_3$—C$_6$H$_4$ | 5T | — | 4C(5.7) | 5C | 5C | 4C (10.7) | 169–170 | CHCl$_3$—MeOH Chromatograph |
| N(CH$_2$)$_3$N(CH$_3$)$_2$ (2-CH$_3$) trans | 4-CF$_3$—C$_6$H$_4$ | 1C (2.7) | 4C (3.7) | 5C | 5C | 5C | 1C (11.0) | 171–172 | CHCl$_3$—MeOH Chromatograph |
| N(CH$_2$)$_3$N(CH$_3$)$_2$ | 4-CF$_3$-3-Cl—C$_6$H$_3$ | 5C | 5C | 5C | 5C | 4C(8.7) | 7.5 | 228–230 | EtOH |
| N(CH$_2$)$_2$N(CH$_2$CH$_3$)$_2$ | 2,4-Cl$_2$—C$_6$H$_3$ | — | — | — | — | — | — | 223–225 | EtOH |
| N(CH$_2$)$_3$N(CH$_3$)$_2$ | 2,4-Cl$_2$—C$_6$H$_3$ | — | — | — | — | — | — | 165–178 | Et$_2$O—Petr. Ether |
| N(CH$_2$)$_4$N(CH$_2$CH$_3$)$_2$ | 2,4-Cl$_2$—C$_6$H$_3$ | — | — | — | — | — | — | 157–161 | EtOH |
| N(CH$_2$)$_3$N(CH$_2$)$_4$ | 2,4-Cl$_2$—C$_6$H$_3$ | — | — | — | — | — | — | 176–177 | DMF |
| N(CH$_2$)$_3$N(CH$_2$CH$_2$OH)$_2$ | 2,4-Cl$_2$—C$_6$H$_3$ | — | — | — | — | — | — | 160–162 | MeOH—CH$_2$Cl$_2$ |
| NCH$_2$CHCH$_2$CH$_3$<br>\|<br>NH—C$_4$H$_9$ | 2,4-Cl$_2$—C$_6$H$_3$ | — | — | — | — | — | — | 173–175 | CH$_2$Cl$_2$—EtOAc |
| NCH$_2$C(CH$_3$)$_2$CH$_2$N(Et)$_2$ | 2,4-Cl$_2$—C$_6$H$_3$ | — | — | — | — | — | — | 153–154 | EtOAc |
| NCH(CH$_3$)(CH$_2$)$_3$N(Et)$_2$ | 2,4-Cl$_2$—C$_6$H$_3$ | — | — | — | — | — | — | 157–160 | EtOH |
| N(CH$_2$)$_7$N(Et)$_2$ | 2,4-Cl$_2$—C$_6$H$_3$ | — | — | — | — | — | — | 135–137 | Triturated CH$_2$Cl$_2$—iso-Propylether |
| N(CH$_2$)$_2$NHCH$_2$CH$_2$OH | 2,4-Cl$_2$—C$_6$H$_3$ | — | — | — | — | — | — | 248–250 | — |
| N(CH$_2$)$_2$NH$_2$ | 2,4-Cl$_2$—C$_6$H$_3$ | — | — | — | — | — | — | 224–225 | DMF—EtOH |

The following examples illustrate the invention.

EXAMPLE 1

Preparation of 7-Chloro-3-(3,4-dichlorophenyl)-1-[[3(dimethylamino)propyl]imino]-1,3,4,10-tetrahydro-10-hydroxy-9(2H)-acridinone.

A solution of 1.4 g of N,N-dimethyl-1,3-propanediamine in 10 ml of ethanol is added dropwise to a stirred, cooled mixture of 4.1 g of 7-chloro-3-(3,4-dichlorophenyl)-3,4-dihydro-10-hydroxy-1,9(2H,10H)acridinedione in 100 ml of ethanol. The mixture is stirred at room temperature overnight and evaporated to dryness in vacuo. The residue is recrystallized from ethanol to give 7-chloro-3-(3,4-dichlorophenyl)1-[[3-(dimethylamino)propyl]imino]-1,3,4,10-tetrahydro-10-hydroxy-9(2H)acridinone; mp 208°–210° C.

By following the above procedure and using N,N-diethylethylenediamine instead of N,N-dimethyl-1,3-propanediamine one obtains 7-chloro-3-(3,4-dichlorophenyl)-1-[[2-(diethylamino)ethyl]imino]-1,3,4,10-tetrahydro-10-hydroxy-9(2H)-acridinone; mp 212°–213° C.

EXAMPLE 2

Preparation of
7-Chloro-1-[[3-(dimethylamino)propyl]imino]-1,3,4,10-tetrahydro-10-hydroxy-3-[4-(trifluoromethyl)phenyl]-9(2H)-acridinone.

To 2.3 g of 7-chloro-3,4-dihydro-10-hydroxy-3-[4-(trifluoromethyl)phenyl]-1,9(2H,10H)-acridinedione in 55 ml of ethanol is added 0.70 g of N,N-dimethyl-1,3-propanediamine in 5 ml of ethanol. The solution is heated to reflux and then allowed to cool to room temperature. The solvent is removed in vacuo and the residue is recrystallized from a mixture of benzene and cyclohexane to give 7-chloro-1-[[3-(dimethylamino)propyl]imino]-1,3,4,10-tetrahydro-10-hydroxy-3-[4-(trifluoromethyl)phenyl]9(2H)-acridinone; mp 130°-135° C.

By following the above procedure and using 7-chloro-3-(2,4-dichlorophenyl)-3,4-dihydro-10-hydroxy-1,9(2H,10H)acridinedione instead of 7-chloro-3,4-dihydro-10-hydroxy3[4-(trifluoromethyl)phenyl]-1,9(2H,10H)-acridinedione one obtains 7-chloro-3-(2,4-dichlorophenyl)-1-[[3-(dimethylamino)propyl]imino]-1,3,4,10-tetrahydro-10hydroxy-9(2H)-acridinone; mp 172°-174° C. from methylene chloride and diisopropyl ether.

EXAMPLE 3

Preparation of
7-Chloro-3-(3,4-dichlorophenyl)-1-[[2(diethylamino)ethyl]imino]-1,3,4,10-tetrahydro-9(2H)acridinone.

A mixture of 2.2 g of 7-chloro-3-(3,4-dichlorophenyl)-3,4-dihydro-1,9(2H,10H)-acridinedione and 6.4 g of N,N-diethylethylenediamine in 150 ml of ethanol is heated under reflux for 1 hr and allowed to cool to room temperature. The reaction mixture is filtered and the crude product recrystallized from N,N-dimethylformamide to give, after drying, 7-chloro-3-(3,4-dichlorophenyl)-1-[[2-(diethylamino)ethyl]imino]1,3,4,10-tetrahydro-9(2H)-acridinone; mp 273°-275° C.

The 7-chloro-3-(3,4-dichlorophenyl)-3,4-dihydro-1,9(2H,10H)-acridinedione starting material can be prepared as follows.

A solution of 14 g of 3,4-dichlorobenzaldehyde in 65 ml of acetone is diluted with 435 ml of water and treated with a solution of 5 g of sodium hydroxide in 50 ml of water. The mixture is stirred for 48 hr, extracted with benzene, dried and concentrated in vacuo to give 3,4-dichlorobenzalacetone as an oil which crystallizes on standing.

A solution of 1.3 g of sodium metal in 30 ml of ethanol is treated with 9 g of diethylmalonate and an ethanolic solution of 12.1 g of 3,4-dichlorobenzalacetone, heated under reflux for 15 min, cooled and concentrated to dryness in vacuo. The residue is treated with 400 ml of water containing 7 g of 80% potassium hydroxide pellets and heated under reflux for 2 hr. Insoluble material is removed and the filtrate is acidified with concentrated sulfuric acid, heated under reflux until carbon dioxide evolution ceases, cooled, filtered, washed with water and dried. Recrystallization from 2-propanol gives 5-(3,4-dichlorophenyl)-1,3-cyclohexanedione; mp 198°-200° C.

A mixture of 3.25 g of 2-nitrobenzaldehyde and 5.5 g of 5-(3,4-dichlorophenyl)-1,3-cyclohexanedione in 20 ml of glacial acetic acid and 20 ml of concentrated hydrochloric acid is heated at 80° C. for 0.5 hr, cooled and poured into 300 ml of water. The solid is digested in hot methanol and dried in vacuo to give 7-chloro-3-(3,4-dichlorophenyl)-3,4-dihydro-10-hydroxy-1,9(2H,-10H)-acridinedione; mp 268°-269° C. (dec).

To 3.0 g of 7-chloro-3-(3,4-dichlorophenyl)-3,4-dihydro-10-hydroxy-1,9(2H,10H)-acridinedione suspended in 30 ml of chloroform is added dropwise 2.1 g of phosphorous trichloride in 20 ml of chloroform. The suspension is warmed at 50° C. for 2 hrs and filtered while warm. The solid is suspended in aqueous ethanol and filtered to give 7-chloro-3-(3,4-dichlorophenyl)-3,4-dihydro-1,9(2H,10H)-acridinedione as a cream solid; mp >325° C.

By following the above procedure and using 7-chloro3-[4-(trifluoromethyl)phenyl]-3,4-dihydro-1,9(2H,10H)acridinedione instead of 7-chloro-3-(3,4-dichlorophenyl)-3,4-dihydro-1,9(2H,10H)-acridinedione and N,N-dimethyl-1,3-propanediamine instead of N,N-diethylenediamine one obtains 7-chloro-1-[[3-(dimethylamino)propyl]imino]-1,3,4,10-tetrahydro-3-[4-(trifluoromethyl)phenyl]-9(2H)-acridinone; mp 211°-213° C. after recrystallization from ethanol.

By following the procedure of Example 3, and using 7-chloro-2-methyl-3-[4-(trifluoromethyl)phenyl]-3,4-dihydro-1,9(2H,10H)-acridinedione instead of 7-chloro-3-(3,4-dichlorophenyl)-3,4-dihydro-1,9(2H,10H)acridinedione and N,N-dimethyl-1,3-propanediamine instead of N,N-diethylenediamine one obtains 7-chloro-1-[[3-(dimethylamino)propyl]imino]-1,3,4,10-tetrahydro2-methyl-3-[4-(trifluoromethyl)phenyl]-9(2H)-acridinone; mp 169°-170° C. after chromatography on silica eluted with chloroform/methanol 7:1.

EXAMPLE 4

Preparation of
7-Chloro-3-(2,4-dichlorophenyl)-1-[[3-(dimethylamino)propyl]imino]-1,3,4,10-tetrahydro9(2H)-acridinone.

A mixture of 3.10 g of 7-chloro-3-(2,4-dichlorophenyl)-3,4-dihydro-1,9(2H,10H)-acridinedione and 1.6 g of N,N-dimethyl-1,3-propanediamine in 125 ml of ethanol is heated under reflux for 1.5 hrs. Approximately 65 ml of solvent is removed by distillation and the resulting turbid solution is filtered. The filtrate is diluted with 50 ml of ether and chilled to 0° C. The solid is collected and recrystallized from a mixture of dichloromethane/ethyl acetate. Dry in vacuo at 80° C. for 4 hrs gives 7-chloro-3-(2,4-dichlorophenyl)-1-[[3-(dimethylamino)propyl]imino]-1,3,4,10-tetrahydro-9(2H)acridinone; mp 168°-170° C.

The 7-chloro-3-(2,4-dichlorophenyl)-3,4-dihydro1,9(2H,10H)-acridinedione starting material can be prepared as follows.

To a solution of 100 g of 2,4-dichlorobenzaldehyde in 440 ml of acetone is added 1 L of water, 70 ml of 50% NaOH and 750 ml of water. The mixture is stirred at room temperature for 65 hrs and then extracted with ether. The extract is dried over MgSO4 and concentrated to 350 ml and cooled to 0° C.

The solid which crystallizes is collected and dried in vacuo to give 1-(2,4-dichlorophenyl)-1-butene-3-one; mp 79°-80° C.

To a solution of 2.3 g of sodium in 200 ml of ethanol is added 15.7 g of diethylmalonate followed by a suspension of 20 g of 1-(2,4-dichlorophenyl)-1-butene-3-one in 100 ml ethanol. The mixture is heated under reflux for 2 hrs and then concentrated to dryness in vacuo. The solid is partitioned between 200 ml water and 200 ml ether. The ether layer is discarded and 20 ml 50% NaOH is added to the aqueous layer which is heated under reflux for 2 hrs. The mixture is filtered and the filtrate is made strongly acidic pH <2 with concentrated sulfuric acid. The mixture is heated on a steam bath for 2 hrs. The resulting solid is collected, pulverized and suspended in 500 ml of 10N sulfuric acid and heated on a steam bath for 2 hrs and cooled to 0° C. The solid is collected, washed with water and recrystallized from a mixture of dimethylformamide and ethyl acetate. Drying in vacuo at 80° C. for 6 hrs gives 5-(2,4-dichlorophenyl)cyclohexane-1,3dione; mp 192°–196° C.

To a suspension of 0.96 g of 50% sodium hydride in 10 ml of N,N-dimethylformamide at −10° C. is added dropwise a solution of 5.14 g of 5-(2,4-dichlorophenyl)-cyclohexan-1,3-dione in 40 ml of N,N-dimethylformamide. During the addition frothing occurs and the temperature rises to 10° C. The mixture is then stirred at room temperature for 1 hr and cooled to 5° C. A solution of 3.96 g of 5-chloroisatoic anhydride in 40 ml of N,N-dimethylformamide is added and stirring is continued at room temperature for 18 hrs and then at 85°–90° C. for 5 hr. The mixture is poured into 1300 ml of ice water containing 10 ml of concentrated hydrochloric acid. The solid is collected, washed with water, and suspended in 200 ml of methanol. The suspension is heated on a steam bath for 0.5 hr, cooled and filtered. The solid is washed with methanol and then with ether and dried in vacuo at 60° C. for 18 hrs to give 7-chloro-3-(2,4-dichlorophenyl)-3,4-dihydro-1,9(2H,10H)-acridinedione; mp 308°–310° C.

What is claimed is:

1. A compound having the formula

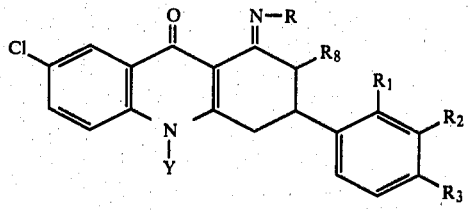

where Y is hydrogen or hydroxy; $R_1$ is hydrogen, fluorine, chlorine, bromine or iodine; $R_2$ and $R_3$ are hydrogen, fluorine, chlorine, bromine, iodine or trifluoromethyl;

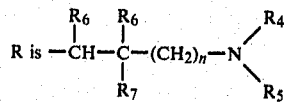

wherein n=0 to 5; $R_4$ and $R_5$ are hydrogen, alkyl containing one to four carbon atoms, —CH$_2$—CH$_2$—OH,

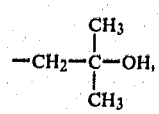

allyl, or $R_4$ and $R_5$ together are (CH$_2$)$_4$ to $_5$, or

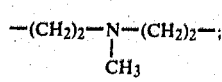

$R_6$ and $R_7$ are hydrogen, methyl, or ethyl; $R_8$ is hydrogen or methyl; and pharmaceutically acceptable salts thereof.

2. A compound according to claim 1 having the formula

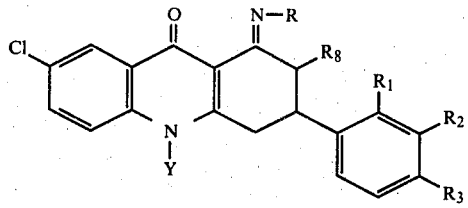

wherein Y is hydrogen or hydroxy; $R_1$ is hydrogen or chlorine; $R_2$ and $R_3$ are hydrogen, chlorine or trifluoromethyl;

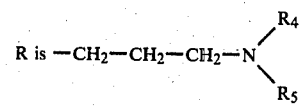

wherein $R_4$ and $R_5$ are hydrogen, $CH_3$ or $C_2H_5$; and pharmaceutically acceptable salts thereof.

3. A compound according to claim 2 which is 7-chloro-3-(2,4-dichlorophenyl)-1-[[3-(dimethylamino)propyl]imino]-1,3,4,10-tetrahydro-9(2H)-acridinone and pharmaceutically acceptable salts thereof.

4. A compound according to claim 2 which is 7-chloro-3-(3,4-dichlorophenyl)-1-[[3-(dimethylamino)propyl]imino]-1,3,4,10-tetrahydro-10-hydroxy-9(2H)-acridinone and pharmaceutically acceptable salts thereof.

5. A compound according to claim 2 which is 7-chloro-3-(3,4-dichlorophenyl)-1-[[2-(diethylamino)ethyl]imino]-1,3,4,10-tetrahydro-10-hydroxy-9(2H)acridinone and pharmaceutically acceptable salts thereof.

6. A compound according to claim 2 which is 7-chloro-1-[[3-(dimethylamino)propyl]imino]-1,3,4,10-tetrahydro-10-hydroxy-3-[4-(trifluoromethyl)phenyl]-9(2H)-acridinone and pharmaceutically acceptable salts thereof.

7. A compound according to claim 2 which is 7-chloro-3-(2,4-dichlorophenyl)-1-[[3-(dimethylamino)propyl]imino]-1,3,4,10-tetrahydro-10-hydroxy-9(2H)acridinone and pharmaceutically acceptable salts thereof.

8. A compound according to claim 2 which is 7-chloro-3-(3,4-dichlorophenyl)-1-[[2-(diethylamino)ethyl]imino]-1,3,4,10-tetrahydro-9(2H)-acridinone and pharmaceutically acceptable salts thereof.

9. A compound according to claim 2 which is 7-chloro-1-[[3-(dimethylamino)propyl]imino]-1,3,4,10-tetrahydro-3-[4-(trifluoromethyl)phenyl]-9(2H)-acridinone and pharmaceutically acceptable salts thereof.

10. A compound according to claim 2 which is 7-chloro-1-[[3-(dimethylamino)propyl]imino]-1,3,4,10-tetrahydro-2-methyl-3-[4-(trifluoromethyl)phenyl]9(2H)-acridinone and pharmaceutically acceptable salts thereof.

11. A pharmaceutical composition for treating malaria in mammals comprising an effective amount of a compound according to claim 1 or a non-toxic pharmaceutically acceptable salt thereof, together with an inert pharmaceutical carrier.

12. A method of treating malaria in mammals comprising the administration of an effective amount of a compound according to claim 1 or non-toxic pharmaceutically acceptable salts thereof.

* * * * *